United States Patent [19]

Stueben et al.

[11] 4,215,076
[45] Jul. 29, 1980

[54] SURFACTANT-PROMOTED ALDOL REACTIONS

[75] Inventors: Kenneth C. Stueben, Bridgewater; Mary L. Deem, Bernardsville, both of N.J.

[73] Assignee: Union Carbide Corporation, New York, N.Y.

[21] Appl. No.: 679,714

[22] Filed: Apr. 23, 1976

[51] Int. Cl.$^2$ .............................................. C07C 47/02
[52] U.S. Cl. ................................ 568/461; 568/388; 568/463; 568/464
[58] Field of Search ................... 260/602, 601 R, 586, 260/593 R

[56] References Cited

U.S. PATENT DOCUMENTS

| | | | |
|---|---|---|---|
| 2,639,295 | 5/1953 | Hagemeyer | 260/601 R |
| 2,863,878 | 9/1958 | Lynn | 260/602 |
| 3,077,500 | 2/1963 | Heine et al. | 260/602 |
| 3,432,557 | 3/1969 | Wile | 260/602 |

*Primary Examiner*—Werren B. Lone
*Attorney, Agent, or Firm*—Bernard Francis Crowe

[57] ABSTRACT

Chemical control of aldol reactions has been achieved by employing a combination of inorganic base-cationic or neutral surfactant catalysts with organic carbonyl compounds.

15 Claims, No Drawings

SURFACTANT-PROMOTED ALDOL REACTIONS

BACKGROUND OF THE INVENTION

This invention pertains to aldol reactions of organic carbonyl compounds and more particularly to their chemical control by the use of a surfactant co-catalyst for said aldol reactions.

L. Claisen reported the preparation of acetaldol from acetaldehyde and aqueous potassium cyanide in 1899. The extension of this experiment to base catalyzed reactions between electron-accepting reactants, such as aldehydes or ketones, and electron-donating components having an active methylene group has led to many industrial chemical syntheses. The aldols obtained can be used as such or as intermediates for further reaction. For example, they can be reduced or dehydrated for use in other syntheses. Thus n-butyraldehyde has been used to make 2-ethylhexanol-1,2-ethylhexanediol (an insect repellant), and 2-ethylbutyric acid.

As with any commercial process there is a continuing demand to improve the economics of each step by increasing yields and increasing reaction rates. The process variables are further complicated when mixtures of carbonyl substrates are used. For example, a mixture of acetaldehyde and butyraldehyde is condensed and dehydrated to produce 2-ethylcrotonal, an intermediate for the synthesis of plasticizers. Since acetaldehyde and butyraldehyde also can undergo self-condensation by themselves, a number of competing reactions takes place leading to the uneconomical diversion of the reactants to undesired products, including 2-hexenal, crotonal, ethylpropylacrolein, and other oligomers plus polymers(rather than dimers). Similar product spreads are obtained when mixed ketones or aldehydes with ketones are subjected to aldol reaction conditions.

It is therefore an object of this invention to provide a means for chemically controlling the reactivities of organic carbonyl compounds in base-catalyzed condensations in order to enhance the yields of desired aldol reaction products and inhibit the formation of by-products, including resins.

It is another object of this invention to increase the reaction rates of the desired reaction paths.

It is still another object to reduce the energy requirements of aldol reactions by operating at lower temperatures than those conventionally in use.

It is still another object to employ co-catalyst surfactants which do not chemically react with the products of the aldol reaction.

SUMMARY OF THE INVENTION

These and other objects have been realized by employing in aldol condensation reactions in addition to an aqueous base catalyst, a co-catalyst, a neutral or cationic surfactant at a molar concentration of about $10^{-4}$ to about $10^{-1}$ based on the moles of carbonyl compounds interacting.

The term cationic surfactant is used in this invention to mean organic compounds which lower surface tension and which possess a positive charge. One preferred class of cationic surfactants may be considered as having been derived from compounds having the general formula:

$$R^{+n}A^{-n}$$

where R can be a moiety with single or multiple onium, e.g., ammonium, phosphonium, arsenonium, and the like centers. For a singly charged ammonium group:

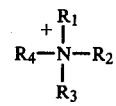

the R groups may be alkyl or aryl. Typical alkyl groups $R_1$, $R_2$, $R_3$, and $R_4$ include octyl, propyl, methyl, and hexadecyl. Anions $A^{-n}$ may be diverse and include the halides ($F^-$, $Cl^-$, $Br^-$, and $I^-$). The surfactants $R^{+n}A^{-n}$ may, or may not, be solvated. A preferred aryl is phenyl.

Representative cationic surfactants can include trioctylmethylammonium chloride, trioctylpropylammonium bromide, cetyltrimethylammonium chloride, and the like.

Another preferred class of cationic surfactants can be derived from salts with hexadecyl chloride and tetraalkyl alkenyl diamines having the general formula:

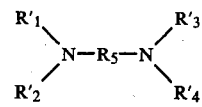

wherein each of $R_1'$, $R_2'$, $R_3'$, and $R_4'$ is an alkyl group having 1 to 18 carbon atoms and $R_5$ is an alkenyl group having 2 or more carbon atoms. Examples of these salts include the dicationic salts of hexadecyl chloride with either N,N,N',N'-tetramethylbutane 1,4-diamine or N,N,N',N'-tetramethylhexane 1,6-diamine.

Neutral surfactants also lower surface tension but neutral surfactants carry no charge.

Exemplary neutral surfactants include polyethoxylated alkyl phenols, carboxamides, alkanolamides having up to 18 carbon atoms, esters of fatty acids, having up to 18 carbon atoms, where the alcohol moiety can be a monohydric one having 1 to 18 carbon atoms, a polyhydric one, such as, alkylene diols or triols having 2 to about 10 carbon atoms, silicone derivatives, including, polyoxyalkylene block copolymers such as L-77, L-520 and the like available from Union Carbide Corp., polydimethylsiloxanes and the like.

While a molar concentration of less than $10^{-4}$ to greater than $10^{-1}$ moles of surfactant can be used, it is preferred to use a molar concentration of about $10^{-4}$ to about $10^{-2}$ moles based on the moles of carbonyl compounds reacting.

The base used as catalyst is not narrowly critical. This term includes the bases commonly used in the prior art, for the aldol condensation reaction. Alkali metal bases such as NaOH, KOH, LiOH and the like are commonly used. However, one also can use such bases as amines, including piperidine and pyridine, metallic alkoxides, such as, sodium ethoxide, metallic carboxylates, including sodium acetate, and salts of other acids, including potassium cyanide, sodium carbonate, and sodium phosphate.

The carbonyl compounds used in this invention include both aldehydes and ketones. These can be saturated or unsaturated aliphatic compounds and can be substituted as long as one reactant possesses one α-hydrogen. Exemplary aliphatic aldehydes include formaldehyde (plus another carbonyl compound), acetaldehyde, propionaldehyde, butyraldehyde, valeraldehyde, dodecanal, octadecanal, 2-ethylhex-2-enal, crotonal, hex-2-enal, 2-ethylbut-2-enal, vinylcrotonal, isobutyral, and the like. Exemplary cycloaliphatic aldehydes include cyclohex-3-enyl aldehyde.

Representative aliphatic ketones include acetone, methyl ethyl ketone, dibutyl ketones, methyl isobutyl ketone, methyl isoamyl ketone, mesityl oxide, 2-methylnon-5-en-4-one, and the like.

The co-catalyst system disclosed herein is effective in either aqueous systems via micellar catalysis or in two-phase, aqueous-organic systems via phase transfer catalysis.

The invention is further described in the examples which follow. All parts and percentages are by weight unless otherwise specified.

EXAMPLE 1

CROSSED ALDOL REACTION OF ACETALDEHYDE AND BUTYRALDEHYDE

A 250 ml. Morton flask fitted with an electric stirrer, an opening closed with a serum stopper, and an addition funnel were positioned in a 35° C. water bath. The flask was charged with 49 ml. of water, 0.1 ml. of an aqueous sodium hydroxide solution (18.75 g. sodium hydroxide in 50 ml. of water), 0.025 ml. of a saturated solution of phenolphthalein in ethanol, and 0.12 g. of trioctylpropylammonium bromide (sufficient to provide a molar concentration of $5 \times 10^{-3}$). The flask contents were mixed by stirring and equilibrated at the bath temperature for about 10 minutes. Then a mixture of 104.8 ml. (1.18 mol.) of n-butyraldehyde (freshly distilled) and 66.7 ml. (1.13 mol.) of acetaldehyde (freshly opened commercial reagent) were added over an interval of about 20 seconds. A dry ice-isopropanol filled cold-finger condenser was rapidly inserted into the remaining neck of the Morton flask and stirring of the reaction mixture was commenced. Whenever the phenolphthalein red color faded, 0.1 ml. aliquots of the sodium hydroxide solution were injected into the mix. After 30 minutes the reaction mixture was quenched by addition of 0.65 ml. of glacial acetic acid. A small aliquot of the upper, organic layer of this mixture was analyzed for its components by gas chromatography.

The crossed condensation product above was immediately transferred to a cracking apparatus designed for dehydrating the aldol products.

The reaction pot of this apparatus was charged with 291 ml. of water, 3.38 ml. of glacial acetic acid, 6.07 g. of sodium acetate, boiling chips, and the aldol product obtained above. After five hours of boiling in the cracking apparatus the distilled and cracked product was analyzed by gas chromatography. The instrument used was an Aerograph A90-P3 fitted with a thermal conductivity detector, a Leeds & Northrup Company Speedomax H recorder, and a Hewlett-Packard 3373B integrator. The ¼ in. diameter stainless steel gas chromatography column was packed with 10% Carbowax 20M (trademark for polyethylene oxide having a molecular weight of about 18,000 to 19,000) on 40/60 Chromosorb T (a polytetrafluoroethylene support sold by Johns-Manville) to a length of 2 meters. The injector temperature was maintained at about 220° C., the column temperature at about 130° C., and the detector temperature at about 200° C.

The analysis data of the cracked aldol reaction product are presented in Table I.

EXAMPLES 2 and 3

CROSSED ALDOL REACTION OF ACETALDEHYDE AND BUTYRALDEHYDE

Example 1 was repeated three times with the exception that the Morton flask was charged with 0.18 g., 0.24 g., and 0 g. of trioctylpropylammonium bromide affording concentrations of $7.5 \times 10^{-3}$ moles, $10.0 \times 10^{-3}$ moles and 0 moles, respectively, of this cationic surfactant. The analysis data of the cracked aldol reaction products are presented in Table I.

EXAMPLE 4

ALDOL REACTION OF BUTYRALDEHYDE n-Butyraldehyde (0.322 g.; 4.47 mol.), 24 ml. of 1.5% aqueous sodium hydroxide and 0.029 g. of trioctylpropylammonium bromide were mixed under nitrogen in a serum-stoppered 25 ml. round-bottomed flask and allowed to interact for five minutes at 30.00° C. ($\pm 0.04°$). The reaction was quenched with 24.0 ml. of glacial acetic acid. Gas chromatography indicated that 90% of the n-butyraldehyde had been converted to its aldol and subsequently dehydrated to 2-ethylhex-2-enal.

In a Control (B), which was a duplicate of Example 4 except that no trioctylpropylammonium bromide was present, only 64% of the dehydrated n-butyraldehyde aldol (2-ethylhex-2-enal) was obtained.

EXAMPLE 5

ALDOL REACTION OF ACETALDEHYDE

Equilibrated with stirring under nitrogen in a serum-stoppered 25 ml. round-bottomed flask at 30.00° ($\pm 0.04°$)C. were 24.0 ml. 1.5% aqueous sodium hydroxide and 0.0786 g. trioctylpropylammonium bromide. Following an equilibration interval of 15 minutes, acetaldehyde (0.255 ml., freshly opened, commercial) was injected. After a reaction interval of two minutes 79.5% of the acetaldehyde was converted to its corresponding aldol (3-hydroxybutanal), based on gas chromatographic analysis.

In a Control (C), which was a duplicate of Example 5 except that no trioctylpropylammonium bromide was present, only 62% of the acetaldehyde was converted to 3-hydroxybutanal after the same reaction interval (two minutes).

EXAMPLE 6

PHASE-TRANSFER CATALYSIS OF n-BUTYRALDEHYDE ALDOL FORMATION

To a 3.0 ml. sample of freshly distilled n-butyraldehyde stirred with 0.0714 g. of trioctylpropylammonium bromide in a 10 ml. flask under nitrogen at 30.00° C.($\pm 0.04°$) was added 1.00 ml. of a 7.4% aqueous sodium hydroxide solution. Thirty minutes after the sodium hydroxide solution was added, 1.5 ml. of glacial acetic acid was injected into the reaction mixture. This quenched mixture was analyzed by gas chromatography with in-line mass spectrometry capability. Of the initial n-butyraldehyde, 8.1% was converted to butyraldol and thence to the corresponding dehydro-aldol (2-ethyl-2-hexenal).

Control D was carried out by repeating Example 6, with the exception that no trioctylpropylammonium bromide surfactant was added. Only 4.3% of the n-butyraldehyde was converted to product.

TABLE I

| Example | [Surfactant*] in water | Initial [Acetaldehyde]:[Butyraldehyde] | Acetaldehyde | Butyraldehyde | Crotonal | 2-Ethylcrotonal trans | 2-Ethylcrotonal cis | 2-Hexenal | Vinylcrotonal | Ethylpropylacrolein | % Accounted for Acetaldehyde | % Accounted for Butyraldehyde |
|---|---|---|---|---|---|---|---|---|---|---|---|---|
| 1 | $5 \times 10^{-3}$ M | 1:1 | 9.7 | 54.7 | 41.9 | 18.4 | 0.2 | 7.1 | 4.2 | 10.9 | 81.5 | 94.2 |
| 2 | $7.5 \times 10^{-3}$ M | 1:1 | 7.3 | 50.1 | 39.3 | 22.4 | 0.2 | 6.5 | 4.8 | 17.6 | 80.5 | 95.6 |
| 3 | $10.0 \times 10^{-3}$ M | 1:1 | 11.3 | 61.2 | 48.3 | 20.0 | 1.9 | 0.7 | 5.0 | 16.3 | 87.2 | 99.0 |
| Control A | None | 1:1 | 20 | 64 | 24.8 | 16.8 | | 3.5 | 1.6 | 7.4 | 66.7 | 90.8 |

*Surfactant = trioctylpropylammonium bromide

In a Control of Example 4, the reaction was run identically to that of Example 4 except that the solution was $2.5 \times 10^{-3}$ M in sodium stearate. No trioctylpropylammonium bromide was used; and in its absence only 70% (maximum) of the butyraldehyde was converted to its aldol, 2-ethyl-3-hydroxyhexanal.

The remarkable effect of using cationic surfactants as co-catalysts in base catalyzed aldol reactions was demonstrated by the finding that the individual rates of condensation of n-butyraldehyde and acetaldehyde in aqueous sodium hydroxide were increased by factors of 9.62 and 4.1, respectively, in the presence of trioctylpropylammonium bromide. Fortuitously, this enhancement of the reaction rate was not accompanied by undesirable side-effects, such as foaming, emulsification, or surfactant decomposition in the reaction vessel.

Although the invention has been described in its preferred forms with a certain degree of particularlity, it is understood that the present disclosure of the preferred forms has been made only by way of example and that numerous changes may be resorted to without departing from the spirit and scope of the invention.

What is claimed is:

1. In the method of condensing aliphatic aldehydes or ketones in the presence of an aqueous base as catalyst to produce an aldol reaction product, the improvement which comprises using as a co-catalyst a neutral or cationic surfactant at a molar concentration of about $10^{-4}$ to about $10^{-1}$ based on the mole of said aliphatic aldehydes or ketones.

2. The method claimed in claim 1 wherein the cationic surfactant is a quaternary ammonium salt.

3. The method claimed in claim 2 wherein the quaternary salt is a tetraalkylammonium halide having 1 to about 18 carbon atoms in each alkyl group.

4. The method claimed in claim 3 wherein the tetraalkylammonium halide is trioctylpropylammonium bromide.

5. The method claimed in claim 3 wherein the tetraalkylammonium halide is trioctylmethylammonium chloride.

6. The method claimed in claim 3 wherein the tetraalkylammonium halide is cetyltrimethylammonium chloride.

7. The method claimed in claim 2 wherein the cationic surfactant is a dicationic salt of an alkyl halide and an N,N,N',N'-tetraalkyl alkylene diamine wherein each alkyl has 1 to about 18 carbon atoms and the alkylene has 2 to 6 carbon atoms.

8. The method claimed in claim 7 wherein the dicationic salt is derived from hexadecyl chloride and N,N,N',N'-tetramethyl hexylene diamine.

9. The method claimed in claim 7 wherein the dicationic salt is derived from hexadecyl chloride and N,N,N',N'-tetramethyl butylene diamine.

10. The method claimed in claim 1 wherein the aliphatic aldehyde is acetaldehyde.

11. The method claimed in claim 1 wherein the aliphatic aldehyde is n-butyraldehyde.

12. The method claimed in claim 1 wherein mixed aliphatic aldehydes are used.

13. The method claimed in claim 12 wherein the mixed aliphatic aldehydes are acetaldehyde and n-butyraldehyde.

14. The method claimed in claim 1 wherein the temperature is about 4° to about 125° C.

15. The method claimed in claim 1 wherein the reaction solvent is water, water mixed with the reactant and/or product carbonyl compounds, or water/reactant/product diluted with an organic solvent.

* * * * *